(12) United States Patent
Ding et al.

(10) Patent No.: US 7,670,985 B2
(45) Date of Patent: Mar. 2, 2010

(54) ACTIVATED CARBON SUPPORTED COBALT BASED CATALYST FOR DIRECTLY CONVERTING OF SYNTHESIS GAS TO MIXED LINEAR ALPHA-ALCOHOLS AND PARAFFINS

(75) Inventors: Yunjie Ding, Dalian (CN); Hejun Zhu, Dalian (CN); Tao Wang, Dalian (CN); Guiping Jiao, Dalian (CN); Yuan Lv, Dalian (CN)

(73) Assignees: Dalian Institute of Chemical Physics, Chinese Academy of Sciences, Dalian (CN); CNOOC New Energy Investment Co., Ltd., Beijing (CN)

( * ) Notice: Subject to any disclaimer, the term of this patent is extended or adjusted under 35 U.S.C. 154(b) by 179 days.

(21) Appl. No.: 11/891,263

(22) Filed: Aug. 9, 2007

(65) Prior Publication Data

US 2008/0293563 A1 Nov. 27, 2008

(30) Foreign Application Priority Data

May 24, 2007 (CN) .................... 2007 1 0099554

(51) Int. Cl.
*B01J 21/18* (2006.01)
*B01J 27/06* (2006.01)
*B01J 23/00* (2006.01)
*B01J 23/02* (2006.01)
*B01J 23/06* (2006.01)
*B01J 23/40* (2006.01)
*B01J 23/74* (2006.01)
*B01J 23/10* (2006.01)
*B01J 23/32* (2006.01)
*B01J 23/58* (2006.01)
*B01J 23/56* (2006.01)
*C01B 31/00* (2006.01)
*C01B 31/02* (2006.01)
*C09C 1/56* (2006.01)

(52) U.S. Cl. .................. 502/180; 502/182; 502/183; 502/184; 502/185; 502/303; 502/304; 502/305; 502/309; 502/312; 502/324; 502/325; 502/328; 502/330; 502/332; 502/340; 502/344; 423/445 R; 423/460

(58) Field of Classification Search ............. 502/180, 502/182–185; 423/445 R, 460
See application file for complete search history.

(56) References Cited

U.S. PATENT DOCUMENTS

| 4,504,600 | A | 3/1985 | Wright et al. |
| 4,513,096 | A | 4/1985 | Connolly et al. |
| 4,551,444 | A | 11/1985 | Lin et al. |
| 4,562,174 | A | 12/1985 | Stiles |
| 4,661,525 | A | 4/1987 | Grazioso et al. |
| 4,675,344 | A | 6/1987 | Conway et al. |
| 4,725,626 | A | 2/1988 | Graham et al. |
| 4,749,724 | A | 6/1988 | Quarderer et al. |
| 4,751,248 | A | 6/1988 | Lin et al. |
| 4,752,622 | A | 6/1988 | Stevens |
| 4,752,623 | A | 6/1988 | Stevens et al. |
| 4,775,696 | A | 10/1988 | Prada-Silva et al. |
| 4,780,481 | A | 10/1988 | Courty et al. |
| 4,824,869 | A | 4/1989 | Prada-Silva et al. |
| 4,825,013 | A | 4/1989 | Quanderer et al. |
| 4,831,060 | A | 5/1989 | Stevens et al. |
| 4,882,360 | A | 11/1989 | Stevens |
| 4,886,651 | A | 12/1989 | Patel et al. |
| 4,943,551 | A | 7/1990 | Dombek |
| 4,980,389 | A | 12/1990 | Hill et al. |
| 4,983,638 | A | 1/1991 | Wong et al. |
| 5,502,019 | A * | 3/1996 | Augustine et al. ........... 502/314 |
| 6,248,796 | B1 | 6/2001 | Jackson et al. |
| 6,720,283 | B2 * | 4/2004 | Ding et al. ................. 502/184 |
| 6,753,353 | B2 | 6/2004 | Jackson et al. |
| 6,765,025 | B2 * | 7/2004 | Ding et al. ................. 518/715 |
| 7,468,396 | B2 * | 12/2008 | Ding et al. ................. 518/715 |
| 2003/0121826 | A1 * | 7/2003 | Ding et al. ................. 518/714 |

FOREIGN PATENT DOCUMENTS

| EP | 0180719 | 5/1986 |
| FR | 635950 | 3/1928 |
| GB | 300294 | 11/1928 |
| GB | 866161 | 4/1961 |

OTHER PUBLICATIONS

R. B. Anderson et al. "Synthesis of Alcohols by Hydrogenation of Carbon Monoxide," Industrial and Engineering Chemistry, vol. 44, No. 10, pp. 2418-2424.

* cited by examiner

*Primary Examiner*—Patricia L Hailey
(74) *Attorney, Agent, or Firm*—Scully, Scott, Murphy & Presser, P.C.

(57) ABSTRACT

The invention provides an activated carbon supported cobalt based catalyst for directly converting of synthesis gas to mixed linear alpha-alcohols and paraffins, comprising cobalt, an activated carbon carrier, a metal promoter which is at least one selected from the group consisting of a zirconium component, a lanthanum component, a cerium component, a chromium component, a vanadium component, a titanium component, a manganese component, a rhenium component, a potassium component, a ruthenium component, a magnesium component and a mixture thereof, wherein the cobalt and the promoter are deposited on the activated carbon carrier or substantially uniformly dispersed therein, and the metal promoter is present in the form of a metal, an oxide or a combination thereof.

11 Claims, No Drawings

ACTIVATED CARBON SUPPORTED COBALT BASED CATALYST FOR DIRECTLY CONVERTING OF SYNTHESIS GAS TO MIXED LINEAR ALPHA-ALCOHOLS AND PARAFFINS

An activated carbon supported cobalt based catalyst for directly converting of synthesis gas to mixed linear alpha-alcohols and paraffins

FIELD OF THE INVENTION

The invention relates to a novel family of a porous carrier supported cobalt based catalyst and their use in the process for the conversion of synthesis gas to mixed linear alpha-alcohols and paraffins (naphtha distillates and diesel fuels) with a carbon number of less than 25 in one-step. Particularly, most part of the compositions of the liquid products from the conversion (ca. 50%) fall into $C_2$-$C_{18}$ mixed linear alpha-alcohols, wherein the high alpha-alcohols ($C_6$-$C_{11}$) are used as the intermediates of plasticizer, the heavy alpha-alcohols ($C_{12}$-$C_{18}$) as the intermediates of detergents, lubricants, surfactants and linear alkylbenzene sulfonates, and the naphtha distillates ($C_5$-$C_{10}$ n-hydrocarbons) were used as a feedstock for cracking into ethylene and the diesel cuts ($C_{10}$-$C_{21}$ n-paraffins) as diesel fuels or their blending stocks.

BACKGROUND OF THE INVENTION

The search for processes to provide alternate feedstocks for fuels and chemicals, and particularly high quality diesel fuels and high value mixed linear alpha-alcohols, has been prompted due to the potential shortage of traditional petroleum reserves, and the increasing instability of international hydrocarbon resources.

Almost as old as the Fischer-Tropsch process for making hydrocarbons is the Fischer-Tropsch process for making alcohols. The Fischer-Tropsch process is carried out by passing a mixture of CO and $H_2$ over a catalyst for the hydrogenation of CO. Numerous catalysts and catalytic methods have been studied in an attempt to provide a viable method for the production of aliphatic alcohols from synthesis gas.

Three main types of processes have been proposed for preparing alcohols from gaseous mixtures comprising carbon monoxide and hydrogen. One of these is a modified Fischer-Tropsch process which involves the use of alkali metal-containing iron based catalysts. Generally, this process suffers from poor selectivity and low productivity. Another process is the iso-butyl synthesis as used in Europe between 1935 and 1945. This process is analogous to the methanol synthesis process and utilizes a similar catalyst, i.e. zinc chromite, modified by addition of an alkali metal salt, at high temperature and high pressure. Typically, the main products from this process comprise methanol (50%), ethanol (20-40%), n-propanol, and higher alcohols which are predominantly non-linear primary and secondary alcohols. The third process was originally assigned to Dow Chemical Company, in which primarily $C_1$ to $C_4$ mixed alcohols are produced in good yield over a supported catalyst based on molybdenum disulfide.

A typical review article related to alcohols preparation is R. B. Anderson et al. "*Industrial and Engineering Chemistry*" vol. 44, No. 10, pp. 2418-2424. A number of catalysts containing zinc, copper, chromium, manganese, thorium and iron, occasionally promoted with alkali or other materials for making various alcohols are listed in this article.

U.S. Pat. No. 4,504,600 provides a CO hydrogenation process for producing alcohols utilizing thallium-promoted iron-based catalysts. A mixture of CO and $H_2$ is selectively converted to liquid $C_6$~$C_{12}$ hydrocarbon containing $C_6$~$C_{12}$ alcohols hydrocarbons in an amount of 4~8 wt. %, and methane in an amount of 1 wt. %, relative to the total produced hydrocarbons, with a $CO_2$ selectivity of 12~18 mol. %.

U.S. Pat. No. 4,513,096 discloses a method for reacting carbon monoxide and hydrogen in a slurry phase to form light hydrocarbons and alcohols, in the presence of iron-containing activated carbon.

U.S. Pat. Nos. 4,551,444 and 4,886,651 provide a modified copper based methanol synthesis catalyst, especially a thoria and zirconia promoted copper catalyst, over which higher yields of $C_1$ to $C_6$ mixed alkanols and hydrocarbons are formed from synthesis gas at reaction conditions.

U.S. Pat. No. 4,562,174 discloses a catalyst comprised of copper and zinc oxides, and optionally manganese oxide or manganese and cobalt oxides and a stabilizer such as chromic, ceric, magnesium or aluminum oxides, over which $C_1$ to $C_6$ mixed alcohols and light hydrocarbons are produced through CO hydrogenation.

U.S. Pat. No. 4,780,481 describes a process for manufacturing a mixture of saturated primary alcohols by reacting carbon monoxide with hydrogen in the presence of a catalyst formed essentially of copper, cobalt and zinc, promoted by alkali and alkaline earth metals and optionally zirconium and rare earth metals.

U.S. Pat. No. 4,943,551 describes a catalyst composition for the production of methanol and higher saturated aliphatic alcohols from synthesis gas. The catalyst consists essentially of copper, thorium, zirconium and an alkali metal.

U.S. Pat. No. 4,725,626 discloses a catalyst and a process for the production of alcohols from CO and $H_2$. The catalyst has the formula: $RuCu_aM_bA_cN_2O_x$, wherein A is an alkali metal or an alkaline earth metal or mixture thereof, and M is Mo and W or mixtures thereof.

U.S. Pat. No. 4,751,248 discloses a process for converting synthesis gas ($H_2$/CO) to aliphatic alcohols containing at least 2 carbon atoms, comprising the steps of passing the synthesis gas firstly through a catalyst zone wherein the catalyst comprises (a) Co metal and/or Co oxide and (b) MgO and/or ZnO (preferably MgO), and then through a catalyst zone wherein the catalyst comprises (c) Cu metal and/or Cu oxide and (d) ZnO.

U.S. Pat. Nos. 4,980,389 and 4,983,638 disclose a catalyst and a method for preparing a mixture of lower aliphatic alcohols. The method includes reacting a mixture of CO and $H_2$ under suitable conditions of temperature and pressure, in the presence of a catalyst composition comprising rhodium, cobalt, molybdenum and a combination of potassium and rubidium.

U.S. Pat. No. 4,749,724 describes a process for forming an alcohol fraction boiling in the boiling range of motor gasoline that is enriched in higher alcohols, comprising the step of contacting a mixture of $H_2$ and CO, and a lower alkanol with a catalyst comprising (1) molybdenum, tungsten or a mixture thereof in free or combined form; (2) an alkali or alkaline earth element; and (3) a support.

U.S. Pat. Nos. 4,675,344 and 4,775,696 state that a method for controlling the ratio of methanol and higher alcohols produced in a process for making mixed alcohols by contacting a $H_2$/CO mixture with a catalyst which contains molybdenum, tungsten or rhenium, said method comprising adjusting the concentration of a sulfur releasing substance in the feedstock.

U.S. Pat. Nos. 4,661,525, 4,752,622, 4,824,869 and 4,825,013 disclose that mixed alcohols are produced from a mixture of CO and $H_2$ using an easily prepared catalyst which comprises a catalyst metal, a co-catalyst metal, and a support, wherein the catalyst metal is molybdenum, tungsten or rhenium, the co-catalyst metal is cobalt, nickel or iron, and the catalyst is promoted by an alkali or alkaline earth metal.

U.S. Pat. Nos. 4,752,623, 4,831,060 and 4,882,360 disclose a process for selectively making $C_1$-$C_6$ alcohols from synthesis gas, comprising the step of contacting a mixture of $H_2$/CO with a catalytic amount of a catalyst wherein the catalyst is consisted of (1) a catalytically active metal, such as molybdenum, tungsten or rhenium; (2) a co-catalytic metal, such as cobalt, nickel, or iron; (3) an alkali or alkaline earth metal; (4) an optional support. The catalyst has to be sulfidized before the contact.

More recently, U.S. Pat. Nos. 6,248,796 and 6,753,353 disclose a method for the production of mixed alcohols by using a sulfidized transition metal catalyst selected from Group VI metals, such as molybdenum or tungsten; nano-sizing the metal catalyst during its synthesis; suspending the catalyst in solvents to form a slurry; adding a sulfur-containing material to extend the catalyst life; and contacting this slurry with a mixture of CO and $H_2$.

Previous catalytic methods have been notably effective for converting CO and $H_2$ feedstocks into hydrocarbons and $C_1$ to $C_6$ alcohols, but none has been particularly effective for providing a substantial yield of a higher aliphatic $C_2$ to $C_{18}$, especially $C_6$ to $C_{18}$ alcohols at a moderate temperature and pressure.

An extensive amount of works have been carried out in order to modify and improve the selectivity of a process for producing $C_6$-$C_{18}$ alcohols, especially $C_6$-$C_{18}$ linear alcohols, particularly under conditions that low methane and $CO_2$ are produced. Such a process is desired since $C_6$-$C_{18}$ linear alcohols are industrially important and used in detergents, surfactants, lubricants and plasticizers.

Thus far, no one has disclosed an activated carbon supported cobalt based catalyst which affords improved yields of paraffins and mixed linear alpha-alkanols from the reaction between carbon monoxide and hydrogen, which minimizes the need for an additional step for the separation of products from the catalyst and which permits the use of high space velocities.

There are two processes for the production of synthetic linear alcohols which are (a) ALFOL® process and EPAL® process, based on the work of Prof. Dr. Ziegler, using organic aluminum compounds and (b) an oxo-process (hydroformylation). The former process involves five steps of: hydrogenation, ethylation, growth reaction, oxidation and hydrolysis, while the latter process consists of the reaction of olefins with a $H_2$/CO gas mixture, in the presence of a suitable catalyst, wherein alpha-olefins yield approximately equal amounts of linear and branched aldehydes, and branched alkenes can also be used in this process due to double-bond being isomerized in the presence of the same catalyst. For a long time, paraffin-based processes were predominant for the production of olefins, especially used for detergents, now ethylene has became a preferable raw material. The principal steps in oxo-process are ethylene oligomerization, isomerization and metathesis.

Naphtha is the most common feedstock sent to naphtha cracking units for the production of ethylene. A typical naphtha feedstock contains a mixture of paraffinic, naphthenic, and aromatic hydrocarbons with varied molecular weight and molecular structure. The compositions of naphtha feedstocks vary considerably, while the composition has a significant impact on ethylene and byproduct yields. Normal and branched paraffins convert to ethylene in a cracker, but the ethylene yield from n-paraffin is much greater than those from others. Naphtha is also used primarily as feedstocks for producing a gasoline component having high octane value via a catalytic reforming process. The naphtha distillates produced from Fischer-Tropsch process contains predominantly n-paraffins having 5 to 11 carbon atoms, which are excellent feedstocks for the production of ethylene.

Clean diesel fuels that contain no or almost no sulfur, nitrogen, or aromatics, are or will likely be demanded largely as diesel fuels or in blending diesel fuels. Clean diesel fuels with some mixed alcohols, having relatively high cetane number, are particularly valuable. Typical petroleum-derived distillates are not clean, in that they typically contain significant amounts of sulfur, nitrogen, and aromatics, and they have relatively low cetane numbers. Clean diesel fuels can be produced from petroleum-derived distillates through severe hydrotreating at great expense. The production of clean, high cetane number distillates from Fischer-Tropsch waxes has been discussed in various literatures, but it is reported in few literatures that the catalyst can be used to directly convert synthesis gas to diesel distillates with high quality and with some level mixed alcohols.

Thus, there is a need for an activated carbon supported cobalt based catalyst that cut off the heavier end of the Schultz-Flory distribution, over which mixed linear alpha-alcohols ($C_2$-$C_{18}$) and the middle distillates (naphtha distillates and diesel fuels) with sulfur-free, nitrogen-free or aromatics-free can be directly synthesized from synthesis gas under moderate condition.

SUMMARY OF THE INVENTION

After intensive study, the inventors find an activated carbon supported cobalt based catalyst that cut off the heavier end of the Schultz-Flory distribution, over which mixed linear alpha-alcohols ($C_2$-$C_{18}$) and the middle distillates (naphtha distillates and diesel fuels) with sulfur-free, nitrogen-free or aromatics-free can be directly synthesized from synthesis gas under moderate condition.

That is, the invention provide an activated carbon supported cobalt based catalyst, comprising 1 to 50 percent by weight of cobalt, based on the activated carbon supported cobalt based catalyst, 10 to 90 percent by weight of an activated carbon carrier, based on the activated carbon supported cobalt based catalyst, and 0.1 to 40 percent by weight of a metal promoter in terms of the metal(s) which is at least one selected from the group consisting of a zirconium component, a lanthanum component, a cerium component, a chromium component, a vanadium component, a titanium component, a manganese component, a rhenium component, a potassium component, a ruthenium component, a magnesium component and a mixture thereof, based on the weight of the activated carbon supported cobalt based catalyst, wherein the cobalt and the promoter are deposited on the activated carbon carrier or substantially uniformly dispersed therein, and the metal promoter is present in the form of a metal, an oxide or a combination thereof.

In one embodiment of the invention, the activated carbon carrier is made from an almond core, a coconut shell, a palm tree wood, or a coal.

In another embodiment of the invention, the activated carbon carrier has a surface area in the range of 200~2000 $m^2$/g, a pore volume of 0.3 to 2.0 ml/g, and a distribution of pore diameter of 4 to 1000 Å.

In a preferred embodiment of the invention, the activated carbon carrier has a surface area in the range of 300~1500 m$^2$/g, a pore volume of 0.35 to 0.75 ml/g, and a distribution of pore diameter of 5 to 500 Å.

In another embodiment of the invention, the catalyst comprises 1 to 40 percent by weights of cobalt, based on the weight of the activated carbon supported cobalt based catalyst.

In a preferred embodiment of the invention, the catalyst comprises 5 to 30 percent by weights of cobalt, based on the weight of the activated carbon supported cobalt based catalyst.

In another embodiment of the invention, the catalyst comprises 0.001 to 30 percent by weight of the metal promoter in terms of the metal(s), based on the weight of the activated carbon supported cobalt based catalyst.

In a preferred embodiment of the invention, the catalyst comprises 0.005 to 10 percent by weight of the metal promoter in terms of the metal(s), based on the weight of the activated carbon supported cobalt based catalyst.

In another embodiment of the invention, the invention provides a process for preparing the catalyst of the present invention, comprising:

(1) supporting the metal promoter from a solution of a salt of the metal component selected from the group consisting of a nitrate, a carbonate, an oxalate, and a chloride with cobalt onto the activated carbon under an atmosphere or a vacuated condition by co-impregnating, stepwise-impregnating, coating, co-precipitating or precipitating, to obtain a supported catalyst X;

(2) drying the supported catalyst X at room temperature for 1 to 10 days, or at 293~353 K for 2 to 48 hours, then at 353 to 373 K for 2 to 48 hours in an argon or a nitrogen flow, and finally calcined at 473 to 937 K for 2 to 48 hours in an argon or a nitrogen flow to obtain a dried catalyst Y, and (3) reducing the dried catalyst Y by flow of a gas consisting of (1) argon or nitrogen and (2) hydrogen having a concentration of 0.1~100% by mole of the gas at a temperature within the range of 473 to 1073 K, at a speed velocity within the range of 300 to 20000 h$^{-1}$, and at a pressure within the range of 0.05 to 2.00 MPa, for 1 to 48 hours.

In one embodiment of the invention, said vacuated condition is less than 1 kPa.

In another embodiment of the invention, said solvent is selecting from the group consisting of deionized water, methanol, ethanol, propanol, or combination thereof.

In another embodiment of the invention, said reduction of catalysts is in-situ activated in the Fischer-Tropsch reactor, or activated in a separate reactor, and then transferred into Fischer-Tropsch reactor in a flow of an inert gas, i.e. argon or nitrogen gas.

In yet another embodiment of the invention, the invention provides a use of the catalyst of claim 1 in a process for directly synthesis of mixed linear alpha-alcohols, naphtha distillates and diesel fuels having carbon numbers of less than 25 as principal distillates from synthesis gas through Fischer-Tropsch synthesis.

Thus, the invention provides activated carbon supported cobalt based catalysts containing Co; activated carbon component; a promoter selected from the group consisting of a Group IVB metal promoter, e.g., Ti, Zr, a Group IIIB metal promoter e.g., La, Ce, a Group VIII metal promoter, e.g., Ru, Rh, an alkali metal promoter, e.g. K, an alkaline earth metal promoter, e.g. Mg, and a mixture thereof, wherein the weight ratio of Co:activated carbon component is 0.05 to 0.4, which exhibits enhanced activity and selectivity toward mixed linear alpha-alcohols ($C_2$-$C_{18}$) and middle distillates during Fischer-Tropsch synthesis. These catalysts also maintain high selectivities for $C_{10}$~$C_{20}$ hydrocarbons and $C_6$-$C_{18}$ mixed linear alpha-alcohols under moderate reaction conditions.

With the activated carbon supported cobalt based catalyst in accordance to the invention, a mixed linear alpha-alcohols being useful as a detergent, a plasticizer, a lubricant and surfactants after proper separation, and a clean naphtha distillates being useful as a feedstock of cracking to ethylene, and a clean distillate with or without some level mixed alcohols being useful as a diesel fuel or as a diesel fuel blend stock and having a cetane number of at least about 60, preferably at least about 70, can be produced, preferably direct from synthesis gas through Fischer-Tropsch process.

Moreover, the invention provides a process for directly preparing mixed linear alpha-alcohols and middle distillates from synthesis gas over the activated carbon supported cobalt based catalyst according to the invention.

DESCRIPTION OF THE PREFERRED EMBODIMENTS

The activated carbon supported cobalt based catalyst according to the invention is prepared from an activated carbon supported cobalt wherein Co: activated carbon carrier weight ratio is about 0.05 to 0.4, containing a metal phase, promoted by zirconium- or lanthanum- or cerium-containing oxide phase, or promoted by a noble metal, or promoted by an alkali- or alkaline earth-containing metal phase. The activated carbon supported cobalt based catalysts are derived from a salt selected from the group consisting of a nitrate, an oxynitrate, a carbonate, an oxalate, chloride, and a mixture thereof, wherein Co:activated carbon carrier weight ratio is in the specified range are expected to give acceptable performance, although it is preferred to operate with a single phase catalyst precursor so as to preclude any irregular behavior in subsequent activation procedures.

A preferred activated carbon carrier has a surface area in the range of about 200-2000 m$^2$/g, preferably 200-1500 m$^2$/g, and a pore volume of about 0.3 to 2.0 ml/g, preferably 0.3 to 1.0 ml/g, a distribution of pore diameter of about 4 to 1000 Å, preferably 10 to 600 Å, a bulk density of about 0.1 to 1.0 g/ml, preferably 0.3 to 0.6 g/ml, and a side crushing strength of about 0.08 to 3.0 kg/mm.

The preferred catalysts comprise a promoter selecting from the group consisting of a Group VIII B non-noble metal promoter, e.g. iron and nickel, a Group IVB metal promoter, e.g., zirconium, titanium, a Group IIIB metal promoter, e.g., cerium, lanthanum, a Group VIII B noble metal promoter, e.g., ruthenium, platinum, rhodium, an alkali and alkaline earth metal promoter, e.g. potassium, and magnesium, and a mixture thereof, supported on a porous support. The porous support is preferably an activated carbon, which is made from an almond core, a coconut shell, a palm tree wood, or a coal.

A promoter selected from the group consisting of a Group IVB metal promoter, e.g., Zr, a Group IIIB metal promoter e.g., La or Ce, a Group VIII B noble metal promoter, e.g., Ru, an alkali or alkaline earth metal promoter, e.g., K or Mg, and a mixture thereof, may be added to the activated carbon carrier before impregnating cobalt component or after impregnating cobalt component, or by co-impregnating with cobalt component, wherein the cobalt component is preferably used as a solution of its nitrate salt, while the zirconium or cerium component is preferably used as a solution of its oxynitrate or nitrate salt although other compounds such as sulfates may also be used, the ruthenium component is preferably used as a solution of its chloride, and the potassium or magnesium component is preferably used as a solution of its nitrate salts.

The catalyst is prepared by co-impregnating or stepwise-impregnating the above metal components from their solutions onto the support, drying at room temperature for 1 to 10 days, or at 353 to 363 K for 2~48 hours, and then at 383 to 393 K for 2~48 hours, and calcined finally at 473 to 1073 K for 2~48 hours.

The cobalt metal is present in the amount of about 30 wt % or less, preferably 5~25 wt. %, while as compared with the Group VIII non-noble metal, the Group IVB, IIIB, IA, or IIA metal promoter, or the Group VIIIB noble metal promoter is usually present in a less amount, e.g., a ratio of 1:2 to about 1:20 relative to the Group VIII non-noble metal.

The activated carbon supported cobalt based catalysts, promoted by the promotor, is first subjected to a pretreatment comprising exposure to an inert gas, such as nitrogen for about 10 hours at 473 to 1073 K, then to reducing gas containing hydrogen or carbon monoxide or mixture thereof. The pretreatment can be conducted in a separate vessel or in the Fischer-Tropsch reactor. Pretreatment in the reactor is preferred in order to eliminate the need for a potentially costly and sensitive transfer step of transferring the catalyst from and to the Fischer-Tropsch synthesis reactor. In situ pretreatment is especially preferred when the catalyst is filled in a fixed bed reactor.

The catalyst of present invention can be filled in fixed bed reactor, and the pretreatment can be in-situ conducted under conditions of a pressure ranging from 0.3-1.5 Mpa, preferably 0.3-1.0 Mpa, a temperature of 473-873 K, and a hydrogen or synthesis gas volume hourly space velocity of 300 to 1500 $h^{-1}$. The reaction operation conditions for directly converting synthesis gas into mixed linear alpha-alcohols and paraffins include a reaction temperature of 393-623 K, a reaction pressure of 0.5-10.0 Mpa, a volume hourly space velocity of the mixture of hydrogen and carbon monoxide of 100-1500 $h^{-1}$.

EXAMPLE 1

10000 grams of activated carbon carrier made from a coconut shell was washed three times with boiling deionized water, and then dried at 393 K for 8 hours (denoted as AC1t). AC1t was characterized to have specific surface area of 1150.5 $m^2/g$ with pore volume of 0.68 $cm^3/g$. Among the total surface area, 25.6% of them were contributed from the mesopore with the range of 4.0~4.8 nm pore size, the rest of them from the micro-pore of the kinds of activated carbon carriers. A solution of zirconium oxynitrate salt was prepared by dissolving 21.62 grams $ZrO(NO_3)_2$ in 500 ml deionized water. The supported zirconium catalyst was prepared by impregnating 354 g activated carbon carrier (AC1t, size 20~40 mesh) described herein with the solution of the zirconium oxynitrate salt under the vacuated conditions (about 0.01 Mpa), drying first at room temperature for 4 days, then at 383 K for 6 hours in an air. A solution of cobalt nitrate salt was prepared by dissolving 315.94 grams $Co(NO_3)_2.6H_2O$ in 500 ml deionized water. The supported Zr-promoted cobalt catalyst was prepared by impregnating the supported zirconium catalyst described herein with the solution of the cobalt nitrate salt under the vacuated conditions (about 0.01 Mpa), drying first at room temperature for 4 days, then at 363 K for 6 hours in an air, and finally calcined at 673 K in a flow argon for 6 hours, to obtain an activated carbon supported cobalt based catalyst, which was called as Catalyst A having a composition of 15Co2Zr/AC1t.

EXAMPLE 2

The same procedures as in example 1 were repeated, except for cobalt nitrate salt instead of zirconyl (IV) nitrate salt being first impregnated, to obtain an activated carbon supported cobalt based catalyst, which was called as Catalyst B having a composition of 2Zr15Co/AC1t.

EXAMPLE 3

The same procedures as in example 1 were repeated, except for 5.31 grams instead of 21.62 grams of zirconyl(IV) nitrate salt and 310.33 grams instead of 315.94 grams of cobalt nitrate salt being used, to obtain an activated carbon supported cobalt based catalyst, which was called as Catalyst C having a composition of 15Co0.5Zr/AC1t.

EXAMPLE 4

The same procedures as in example 1 were repeated, except for 44.32 grams instead of 21.62 grams of zirconyl(IV) nitrate salt and 323.74 grams instead of 315.94 grams of cobalt nitrate being used, to obtain an activated carbon supported cobalt based catalyst, which was called as Catalyst D having a composition of 15Co4Zr/AC1t.

EXAMPLE 5

The same procedures as in example 1 were repeated, except for 20.40 grams instead of 21.62 grams of zirconyl(IV) nitrate salt and 198.66 grams instead of 315.94 grams of cobalt nitrate salt being used, to obtain an activated carbon supported cobalt based catalyst, which was called as Catalyst E having a composition of 10Co2Zr/AC1t.

EXAMPLE 6

The same procedures as in example 1 were repeated, except for 23.01 grams instead of 21.62 grams of zirconyl(IV) nitrate salt and 448.25 grams instead of 315.94 grams of cobalt nitrate salt being used, to obtain an activated carbon supported cobalt based catalyst, which was called as Catalyst F having a composition of 20Co2Zr/AC1t.

EXAMPLE 7

A solution of zirconium and ruthenium salts were prepared by dissolving 21.76 grams $ZrO(NO_3)_2$ and 5.65 grams $RuCl_3.xH_2O$ (Rh 38%) in 500 ml deionized water. The supported zirconium and ruthenium catalyst was prepared by impregnating 354 g activated carbon carrier (AC1t, size 20~40 mesh) described herein with the solution of the zirconium and ruthenium salts under the vacuated conditions (about 0.01 Mpa), drying first at room temperature for 4 days, then at 383 K for 6 hours in an air. A solution of cobalt nitrate salt was prepared by dissolving 317.85 grams $Co(NO_3)_2.6H_2O$ in 500 ml deionized water. The supported Zr- and Ru-promoted cobalt catalyst was prepared by impregnating the supported zirconium and ruthenium catalyst described herein with the solution of the cobalt salt under the vacuated conditions (about 0.01 Mpa), drying first at room temperature for 4 days, then at 363 K for 6 hours in an air, and finally calcined at 673 K in a flow argon for 6 hours, to obtain an activated carbon supported cobalt based catalyst, which was called as Catalyst G having a composition of 15Co2Zr0.5Ru/AC1t.

EXAMPLE 8

A solution of zirconium and lanthanum salts were prepared by dissolving 10.75 grams $ZrO(NO_3)_2$ and 6.61 grams $La(NO_3)_3.6H_2O$ in 500 ml deionized water. The supported zirconium and lanthanum catalyst was prepared by impregnating 354 g activated carbon carrier (AC1t, size 20~40 mesh) described herein with the solution of the zirconium and lanthanum salts under the vacuated conditions (about 0.01 Mpa), drying first at room temperature for 4 days, then at 383 K for 6 hours in an air. A solution of cobalt nitrate salt was prepared by dissolving 314.05 grams $Co(NO_3)_2.6H_2O$ in 500 ml deionized water. The supported Zr- and La-promoted cobalt catalyst was prepared by impregnating the supported zirconium and lanthanum catalyst described herein with the solution of the cobalt salt under the vacuated conditions (about 0.01 Mpa), drying first at room temperature for 4 days, then at 363 K for 6 hours in an air, and finally calcined at 673 K in a flow argon for 6 hours, to obtain an activated carbon supported cobalt based catalyst, which was called as Catalyst H having a composition of 15Co1Zr0.5La/AC1t.

EXAMPLE 9

The same procedures as in example 3 were repeated, except for an activated carbon (untreated with boiling deionized water). AC2 was made from an almond core instead of a coconut shell. AC2 was characterized to have specific surface area of 1068.7 $m^2/g$ with pore volume of 0.65 $cm^3/g$. Among the total surface area, 20.2% of them were contributed from the meso-pore with the range of 4.0~4.8 nm pore size, the rest of them from the micro-pore of the kinds of activated carbon carriers. AC2 was used as the activated carbon carrier, to obtain an activated carbon supported cobalt based catalyst, which was called as Catalyst I having a composition of 15Cu0.5Zr/AC2.

EXAMPLE 10

10000 grams of activated carbon carrier made from an almond core was washed three times with boiling deionized water, and then dried at 393 K for 8 hours (denoted as AC2t). The same procedures as in example 3 were repeated, except for AC2t instead of AC1t being used as the activated carbon carrier, to obtain an activated carbon supported cobalt based catalyst, which was called as Catalyst J having a composition of 15Cu0.5Zr/AC2t.

EXAMPLE 11

The same procedures as in example 10 were repeated, except for 13.14 grams lanthanum nitrate salt instead of 5.31 grams zirconyl(IV) nitrate salt and 312.18 grams instead of 310.33 gram of cobalt nitrate salt being used, to obtain an activated carbon supported cobalt based catalyst, which was called as Catalyst K having a composition of 15Co1La/AC2t.

EXAMPLE 12

The same procedures as in example 11 were repeated, except for 26.43 grams cerium nitrate salt instead of 13.14 grams lanthanum nitrate salt and 315.94 gram instead of 312.18 grams cobalt nitrate salt being used, to obtain an activated carbon supported cobalt based catalyst, which was called as Catalyst L having a composition of 15Co2Ce/AC2t.

EXAMPLE 13

The same procedures as in example 12 were repeated, except for 1.08 gram potassium nitrate salt instead of 26.43 g cerium nitrate salt and 308.86 gram instead of 315.94 gram cobalt nitrate salt being used, to obtain an activated carbon supported cobalt based catalyst, which was called as Catalyst M having a composition of 15Co0.1K/AC2t.

EXAMPLE 14

The same procedures as in example 8 were repeated, except for an AC2t instead of AC1t, 21.76 g zirconyl(IV) nitrate salt, 317.85 gram cobalt nitrate salt and 5.55 gram potassium nitrate salt instead of 10.75 gram zirconyl(IV) nitrate salt, 314.05 gram cobalt nitrate salt and, 6.61 gram lanthanum nitrate salt, respectively, being used, to obtain an activated carbon supported cobalt based catalyst, which was called as Catalyst N having a composition of 15Co2Zr0.1K/AC2t.

EXAMPLE 15

The same procedures as in example 13 were repeated, except for 0.11 gram potassium nitrate salt and 308.54 gram cobalt nitrate salt instead of 1.08 gram potassium nitrate salt and 308.87 gram cobalt nitrate salt, respectively, being used, to obtain an activated carbon supported cobalt based catalyst, which was called as Catalyst O having a composition of 15Cu0.01K/AC2t.

EXAMPLE 16

The same procedures as in example 15 were repeated, except for 44.45 g magnesium nitrate salt and 312.18 gram cobalt nitrate salt instead of 0.11 g potassium nitrate salt and 308.54 gram cobalt nitrate salt, respectively, being used, to obtain an activated carbon supported cobalt based catalyst, which was called as Catalyst P having a composition of 15Co1Mg/AC2t.

EXAMPLE 17

10000 grams of activated carbon carrier made from a coal was washed three times with boiling deionized water, and then dried at 393 K for 8 hours (denoted as AC3t). AC3t was characterized to have specific surface area of 586.8 $m^2/g$ with pore volume of 0.57 $cm^3/g$. Among the total surface area, 5.6% of them were contributed from the meso-pore with the range of 4.0~4.8 nm pore size, the rest of them from the micro-pore of the kinds of activated carbon carriers. The same procedures as in example 3 were repeated, except for AC3t instead of AC1t being used as the activated carbon carrier, to obtain an activated carbon supported cobalt based catalyst, which was called as Catalyst Q having a composition of 15Co2Zr/AC3t.

EXAMPLE 18

Activation of 3.0 grams each of catalyst A-Q was carried out in a fixed bed reactor at the following conditions: T=673 K, P=0.2 Mpa, GHSV=1000 $h^{-1}$ in a flow of a mixture of 10% $H_2$ and 90% $N_2$ before the Fischer-Tropsch reaction. The temperature of the catalyst bed was first cooled down to 423 K, then the synthesis gas is introduced into the fixed bed reactor, the pressure of synthesis gas was adjusted up to 3.0 Mpa, and the velocity speed of synthesis gas was controlled at 1300 h$^{-1}$, then the reaction temperature was slowly enhanced up to 493 K. The liquid products had been collected for 50 hours started at TOS (time on stream)=24 hours. The results of experiments were shown in table 1.

TABLE 1

Results of Fischer-Tropsch reaction over activated carbon supported cobalt based catalysts

| | | | Selectivity mol. % | | | | | Distribution of products in oil liquid phase, wt % | | | |
|---|---|---|---|---|---|---|---|---|---|---|---|
| Catalysts | Composition | CO Conversion % | methane | $CO_2$ | alpha-alcohols | olefins | $C_2^+$ Paraffins | methanol | $C_{2-18}$ alpha-alcohols | olefins | Paraffins |
| A | 15Co2Zr/AC1t | 30.2 | 21.1 | 3.0 | 16.2 | 17.7 | 42.0 | 4.2 | 26.3 | 3.7 | 65.8 |
| B | 2Zr15Co/AC1t | 26.3 | 24.6 | 3.4 | 12.0 | 16.8 | 43.2 | 3.6 | 28.9 | 3.1 | 64.4 |
| C | 15Co0.5Zr/AC1t | 22.4 | 26.7 | 3.8 | 14.1 | 12.8 | 42.6 | 5.5 | 21.9 | 2.1 | 70.5 |
| D | 15Co4Zr/AC1t | 42.4 | 20.3 | 2.8 | 11.3 | 19.8 | 45.8 | 2.5 | 19.2 | 5.1 | 73.2 |
| E | 10Co2Zr/AC1t | 19.1 | 18.6 | 1.7 | 19.9 | 13.7 | 46.1 | 2.3 | 30.3 | 5.5 | 61.9 |
| F | 20Co2Zr/AC1t | 39.1 | 25.6 | 1.2 | 18.9 | 15.8 | 38.5 | 4.7 | 27.3 | 3.5 | 64.5 |
| G | 15Co2Zr0.5Ru/AC1t | 38.9 | 17.3 | 0.5 | 26.8 | 14.4 | 41.0 | 2.1 | 35.5 | 6 | 56.4 |
| H | 15Co1Zr0.5La/AC1t | 62.1 | 11.2 | 2.8 | 38.3 | 6.5 | 41.2 | 5.3 | 50.3 | 3.5 | 40.9 |
| I | 15Co0.5Zr/AC2 | 34.3 | 30.7 | 2.4 | 19.3 | 13.9 | 33.7 | 5.1 | 33.4 | 2.3 | 59.2 |
| J | 15Co0.5Zr/AC2t | 23 | 31.7 | 2.8 | 27.4 | 12.8 | 25.3 | 9.1 | 63.5 | 1.3 | 26.1 |
| K | 15Co1La/AC2t | 13.9 | 46.1 | 4.2 | 7.8 | 17.8 | 24.1 | 14.9 | 65.2 | 1.1 | 18.8 |
| L | 15Co2Ce/AC2t | 66.1 | 29.1 | 3.3 | 24.7 | 14.4 | 28.5 | 9.5 | 52.8 | 3.6 | 34.1 |
| M | 15Co0.1K/AC2t | 8.9 | 38.6 | 4.6 | 9.6 | 24.5 | 22.7 | 15 | 62.6 | 0.9 | 21.5 |
| N | 15Co2Zr0.1K/AC2t | 6.6 | 19.3 | 3 | 22.8 | 19.4 | 35.5 | 5.1 | 53.6 | 2.1 | 39.2 |
| O | 15Co0.01K/AC2t | 8.8 | 20.6 | 3.5 | 19.7 | 26.7 | 29.8 | 6.7 | 59.7 | 1.1 | 32.5 |
| P | 15Co1Mg/AC2t | 14.0 | 29.9 | 3.9 | 21.3 | 20.2 | 24.7 | 8.9 | 51.1 | 3.9 | 36.1 |
| Q | 15Co2Zr/AC3t | 15.8 | 34.9 | 4.1 | 19 | 19.9 | 22.1 | 8.3 | 45.4 | 1.5 | 44.8 |

Reaction conditions: T = 493 K; P = 3.0 MPa; GHSV = 1300 h$^{-1}$; The samples had been collected for 50 hours from TOS = 24 hour.

What is claimed is:

1. An activated carbon supported cobalt based catalyst, comprising
   1 to 50 percent by weight of cobalt, based on the activated carbon supported cobalt based catalyst,
   10 to 90 percent by weight of an activated carbon carrier, based on the activated carbon supported cobalt based catalyst, and
   0.1 to 40 percent by weight of a lanthanum component, and a metal promoter in terms of the metal(s) which is at least one selected from the group consisting of a zirconium component, a cerium component, a chromium component, a vanadium component, a titanium component, a manganese component, a rhenium component, a potassium component, a ruthenium component, a magnesium component and a mixture thereof, based on the weight of the activated carbon supported cobalt based catalyst,
   wherein the cobalt and the promoter are deposited on the activated carbon carrier or substantially uniformly dispersed therein, and
   the lanthanum component and the metal promoter are present in the form of a metal, an oxide or a combination thereof, wherein the activated carbon carrier is made from a coconut shell.

2. The catalyst of claim 1, wherein the activated carbon carrier has a surface area in the range of 200~2000 m$^2$/g, a pore volume of 0.3 to 2.0 ml/g, and a distribution of pore diameter of 4 to 1000 Å.

3. The catalyst of claim 2, wherein the activated carbon carrier has a surface area in the range of 300~1500 m$^2$/g, a pore volume of 0.35 to 0.75 ml/g, and a distribution of pore diameter of 5 to 500 Å.

4. The catalyst of claim 1, which comprises 1 to 40 percent by weight of cobalt, based on the weight of the activated carbon supported cobalt based catalyst.

5. The catalyst of claim 4, which comprises 5 to 30 percent by weight of cobalt, based on the weight of the activated carbon supported cobalt based catalyst.

6. The catalyst of claim 1, which comprises 0.001 to 30 percent by weight of the lanthanum component and the metal promoter in terms of the metal(s), based on the weight of the activated carbon supported cobalt based catalyst.

7. The catalyst of claim 6, which comprises 0.005 to 10 percent by weight of the lanthanum component and the metal promoter in terms of the metal(s), based on the weight of the activated carbon supported cobalt based catalyst.

8. A process for preparing an activated carbon supported cobalt based catalyst, comprising:
   1 to 50 percent by weight of cobalt, based on the activated carbon supported cobalt based catalyst,
   10 to 90 percent by weight of an activated carbon carrier, based on the activated carbon supported cobalt based catalyst, and
   0.1 to 40 percent by weight of a metal promoter in terms of the metal(s) which is at least one selected from the group consisting of a zirconium component, a lanthanum component, a cerium component, a chromium component, a vanadium component, a titanium component, a manganese component, a rhenium component, a potassium component, a ruthenium component, a magnesium component and a mixture thereof, based on the weight of the activated carbon supported cobalt based catalyst,
   wherein the cobalt and the promoter are deposited on the activated carbon carrier or substantially uniformly dispersed therein, and
   the metal promoter is present in the form of a metal, an oxide or a combination thereof,
   wherein the activated carbon carrier is made from a coconut shell, the process comprising:
   (1) supporting the metal promoter from a solution of a salt of the metal promoter selected from the group consisting of a nitrate, a carbonate, an oxalate, and a chloride with cobalt and a solvent onto the activated carbon under an atmosphere or a vacuated condition by co-impregnating, stepwise-impregnating, coating, co-precipitating or precipitating, to obtain a supported catalyst X;

(2) drying the supported catalyst X at room temperature for 1 to 10 days, or at 293~353 K for 2 to 48 hours, then at 353 to 373 K for 2 to 48 hours in an argon or a nitrogen flow, and finally calcined at 473 to 937 K for 2 to 48 hours in an argon or a nitrogen flow to obtain a dried catalyst Y, and (3) reducing the dried catalyst Y by flow of a gas consisting of (1) argon or nitrogen and (2) hydrogen having a concentration of 0.1~100% by mole of the gas at a temperature within the range of 473 to 1073 K, at a speed velocity within the range of 300 to 20000 $h^{-1}$, and at a pressure within the range of 0.05 to 2.00 MPa, for 1 to 48 hours.

9. The process of claim 8, wherein said vacuated condition is less than 1 kPa.

10. The process of claim 8, wherein said solvent is selecting from the group consisting of deionized water, methanol, ethanol, propanol, or combination thereof.

11. The process of claim 8, wherein said reduction of catalysts is in-situ activated in a Fischer-Tropsch reactor, or activated in a separate reactor, and then transferred into Fischer-Tropsch reactor in a flow of an inert gas, i.e. argon or nitrogen gas.

* * * * *